United States Patent [19]
Numano et al.

[11] Patent Number: 5,447,508
[45] Date of Patent: Sep. 5, 1995

[54] DISPOSABLE DIAPERS

[75] Inventors: Kazuki Numano; Tohru Sasaki, both of Kawanoe, Japan

[73] Assignee: Uni-Charm Corporation, Ehime, Japan

[21] Appl. No.: 210,996

[22] Filed: Mar. 21, 1994

[30] Foreign Application Priority Data

Mar. 30, 1993 [JP] Japan .................................. 5-071938

[51] Int. Cl.$^6$ .................................................. A61F 13/15
[52] U.S. Cl. .................................. 604/385.2; 604/394
[58] Field of Search ............................ 604/385.1–392; 2/401

[56] References Cited

U.S. PATENT DOCUMENTS 5,055,103  10/1991  Nomura et al. .................. 604/385.2

FOREIGN PATENT DOCUMENTS 0487921  6/1992  European Pat. Off. .......... 604/385.2
4317650  11/1992  Japan ................................ 604/385.2
0576567  3/1993  Japan ................................ 604/385.2
2235125  2/1991  United Kingdom .

*Primary Examiner*—Randall L. Green
*Assistant Examiner*—K. M. Reichle
*Attorney, Agent, or Firm*—Lowe, Price, Leblanc & Becker

[57] ABSTRACT

A disposable diaper includes a backsheet and a topsheet connected to form front and rear bodies. First and second elastic members are attached to the backsheet around first and second leg-openings thereof to so that the first elastic member provided around the first leg-opening further extends along a curved course into the front and rear bodies and terminates at one side edge of front and rear bodies. The second elastic member provided around the second leg-opening further extends along a curved course into the front and rear bodies and terminates at the other side edge of the front and rear bodies. The respective elastic members comprise a plurality of elastic threads extending in parallel with one another.

3 Claims, 2 Drawing Sheets

DISPOSABLE DIAPERS

BACKGROUND OF THE INVENTION

The present invention relates to a disposable diaper utilized for the absorption and containment of urine and other body excretions.

FIG. 2 of the accompanying drawings is a perspective view of a conventional disposable diaper 50. The diaper 50 comprises a liquid-permeable topsheet 2, a liquid impermeable backsheet 3, a liquid-absorbent core 4 sandwiched therebetween, elastic members 51 provided along right and left side edges of a crotch zone destined to define right and left leg-openings, and elastic members 52 provided along longitudinally opposite ends of front and rear bodies which are destined to define a waist-opening. The rear body 6 is provided along transversely opposite side edges with tape fasteners 8 by which the rear body 6 is fastened to the front body 5. The crotch zone 7 is a longitudinally intermediate zone of said front and rear bodies.

One example of a conventional disposable diaper is disclosed in Japanese patent application Disclosure No. 1992-289201. Specifically, the diaper therein is a disposable diaper pants type diaper in which elastic members are attached to front and rear bodies over a wide extent so as to extend toward a waist line of the diaper and thereby these front and rear bodies are provided over the wide extent with elasticity.

When the conventional disposable diaper of FIG. 2 is worn, the side edges of the crotch zone destined to define the leg-openings and the longitudinally opposite ends destined to define the waist-opening come in close contact with the wearer's skin. However, portions of the front and rear bodies which are remote from the longitudinally opposite ends and closer to the crotch zone do not fit well making it difficult to rapidly absorb urine.

To solve such a problem, the technique has already been proposed, according to which suitable elastic material is used for a topsheet and/or a backsheet of the diaper. However, such material is relatively expensive and necessarily increases material cost.

The technique disclosed in Disclosure No. 1992-289201 intends to solve this problem by employing relatively inexpensive rubber threads. However, according to this technique, a plurality of rubber threads are transversely attached to the diaper to serve as an elastic waist member and plural rubber threads are attached to the diaper longitudinally thereof to elasticize the leg-openings. Attachment of the rubber threads to the diaper in these two directions requires two separate processes which both prolongs and increases production costs.

It a principal object of the invention to solve these prior art problems with an improved arrangement such that elastic members comprising inexpensive elastic thread members extend from respective leg-openings along a curved course over front and rear bodies so that the elastic member provided around the left leg-opening further extends to the right side edge of the waist-opening and the elastic member provided around the right leg-opening further extends to the left side edge of the waist-opening.

SUMMARY OF THE INVENTION

The object set forth above is achieved, according to the invention, by a disposable diaper comprising a liquid-permeable topsheet, a liquid-impermeable backsheet, a liquid-absorbent core sandwiched therebetween, and elastic members provided around a waist-opening and leg-openings, respectively. In accordance with the invention the elastic members provided around each of said leg-openings comprises a first elastic member and a second elastic member including a plurality of elastic threads further extending in parallel with one another from transversely opposite edges of a crotch zone into the front and rear bodies. The first elastic member associated with the left leg-opening further extends along a curved course into the front and rear bodies and terminates at one side edge of the front and rear bodies while the second elastic member associated with a second leg-opening further extends along a curved course into the front and rear bodies and terminates at the other side edge of the front and rear bodies.

With the disposable diaper constructed as described, the first elastic member provided around the first leg-opening further extends along the curved course into each body to one side edge of the front and rear bodies and the second elastic member provided around the second leg-opening further extends along the curved course into each body to the other side edge of the front and rear bodies so that the front and rear bodies may be stretchable in the direction of the front and rear bodies, respectively. Consequently, the diaper of the invention allows not only the front and rear waists but also the portion of the front and rear bodies extending from the front and rear waists to the crotch zone to be reliably brought in close contact with the wearer's skin when the diaper is worn.

BRIEF DESCRIPTION OF THE DRAWINGS

A disposable diaper of the invention will be described more in detail with reference to the accompanying drawings, in which.

It should be understood that parts common in FIG. 1 to those of the conventional diaper shown in FIG. 2 are designated with the same reference numerals.

PREFERRED EMBODIMENT OF THE INVENTION

Figure 1:
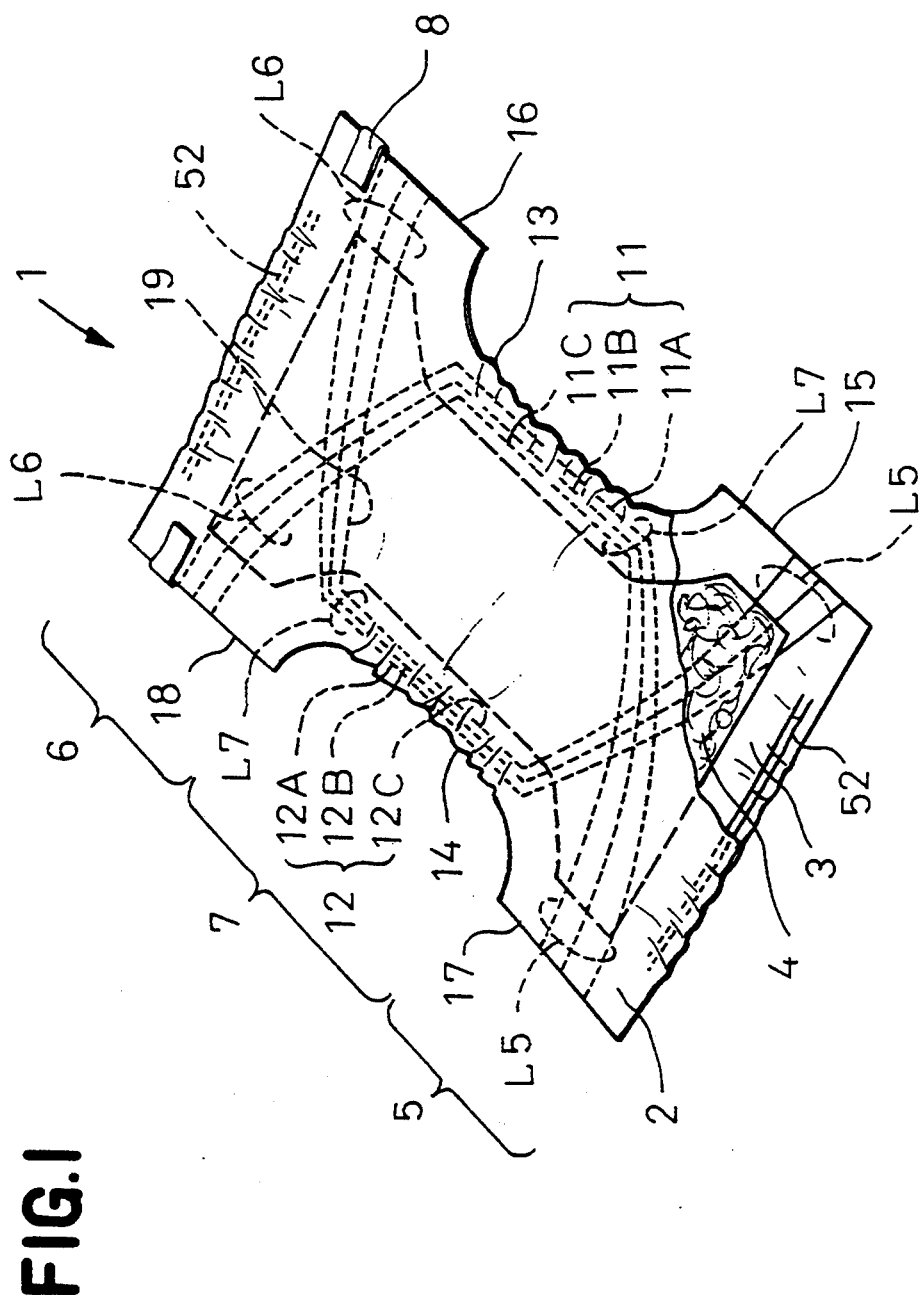
FIG. 1 is a perspective view, partially broken away, of a disposable diaper of the invention.
Figure 2:
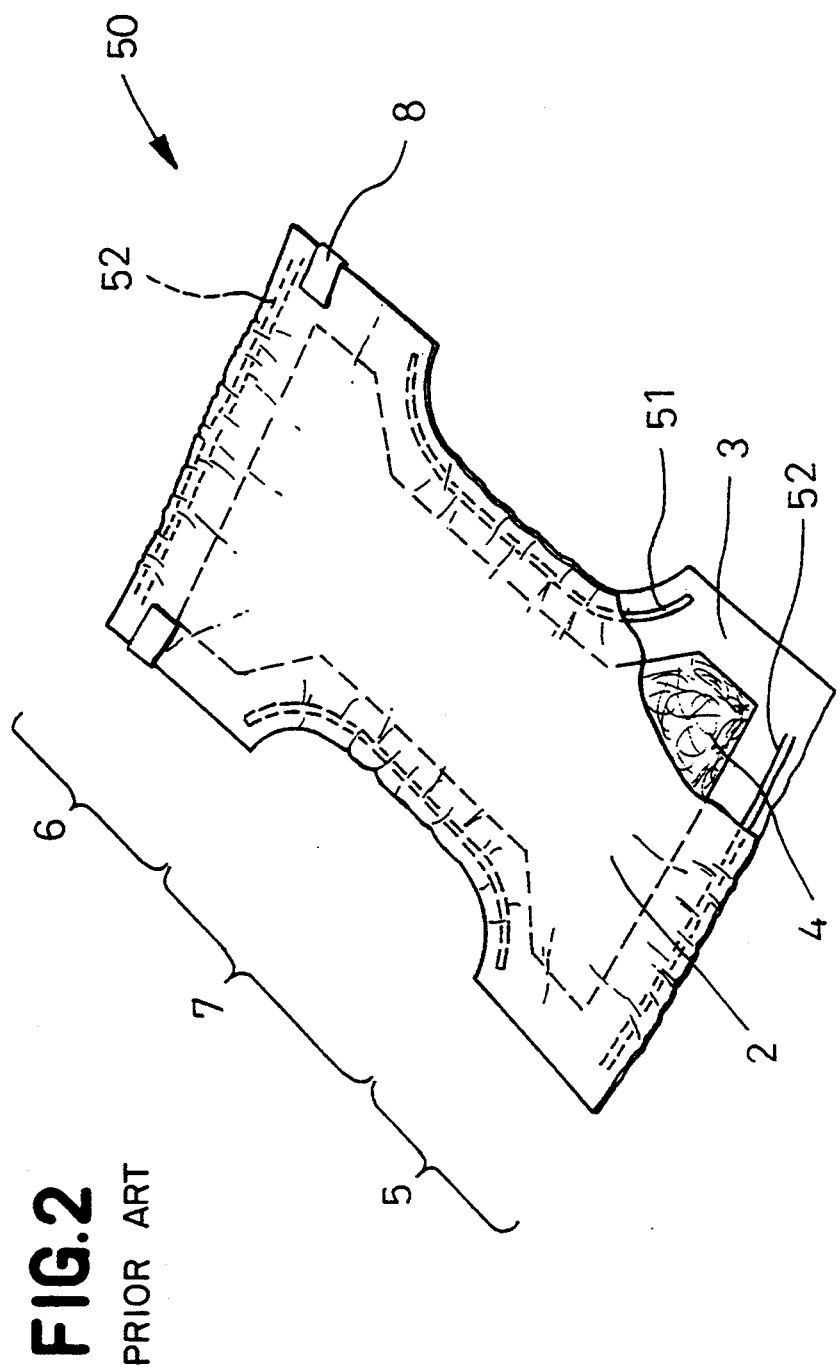
FIG. 2 is a view similar to FIG. 1 of a conventional disposable diaper of prior art.

Referring to FIG. 1, a disposable diaper 1 of the invention comprises a liquid-permeable topsheet 2, a liquid-impermeable backsheet 3, a liquid-absorbent core 4 sandwiched therebetween, defining front and rear bodies 5, 6, respectively, of which longitudinally outer ends are provided with elastic members 52, with tape fasteners 8 attached to the rear body 6 on transversely opposite longitudinal side edges 16, 18 at the level of a waist line of the diaper 1.

Diaper 1 further includes elastic members 11, 12 extending in parallel with transversely opposite side edges 13, 14 of a crotch zone 7 which are destined to define respective leg-openings. Each of the elastic members 11, 12 comprises a plurality of elastic threads 11A, 11B, 11C and 12A, 12B, 12C, respectively, which further extend from the crotch zone 7 into both the front and rear bodies 5, 6. The elastic threads 11A, 11B, 11C starting from around a left leg-opening of the diaper 1 are curved at longitudinally opposite ends of the crotch zone 7 so as to extend into the front and rear bodies 5, 6 and terminate at right side edges 17, 18 of these bodies which are destined to define a portion of a waist-opening of the diaper 1. The rubber-like elastic threads 12A, 12B, 12C starting from around a right leg-opening of the diaper 1 are similarly curved so as to extend into the respective bodies and terminate at left side edges 15, 16 thereof which are destined to define the other portion of the waist-opening. In consequence, the elastic threads 11A, 11B, 11C cross the elastic threads 12A, 12B, 12C on longitudinal center areas of the front and rear bodies 5, 6, respectively. The elastic threads are bonded to an inner surface of the backsheet 3 in their stretched condition and, in the crotch zone 7, extend outside respective lateral side edges of the liquid-absorbent core 4 substantially in parallel to one another. Thus, portions of the elastic threads 11A, 11B, 11C and 12A, 12B, 12C extending over the crotch zone 7 and the front and rear bodies 5, 6 define a loop-shaped seal 19 surrounding a central zone of the diaper. In the front and rear bodies 5, 6, the elastic threads follow a curve extending from the respective leg-openings to the respective side edges of the respective front and rear bodies with an interthread spacing of these elastic threads progressively widening in the direction of the respective side edges of the front and rear bodies. Referring to FIG. 1, portions of the respective elastic threads extending over the crotch zone 7 are generally designated by L7 and portions extending over the front and rear bodies 5, 6 are generally designated by L5, L6, respectively. An elongation stress of the portions L7 is adjusted to be higher than those of the portions L5, L6.

When the diaper 1 as described above is worn, the waist-opening comes in close contact with the wearer's skin under the effect of the elastic member 52. The leg-openings also come in close contact with the skin under the effect of the portions L7 of the elastic threads and the front and rear bodies 5, 6 come in close contact with the skin under the contractile force exerted by the portions L5, L6 of the elastic threads toward the waist line. In view of the fact that the liquid-absorbent core 4 is relatively rigid, the effect of the contractile force may be enhanced by an arrangement such that the liquid-absorbent core 4 is not bonded to the backsheet 3 in the front and rear bodies 5, 6. If necessary, the liquid-absorbent core 4 may be bonded to the topsheet 2 or bonded to the backsheet 3 only in the crotch zone 7.

Topsheet 2 may be formed of nonwoven fabric or open-cell plastic film. Backsheet 3 may be formed of plastic film, for example, made of polyethylene, and liquid-absorbent core 4 may be formed, for example, from a mixture of fluff pulp and high absorption polymer powders.

Elastic threads 11A, 11B, 11C and 12A, 12B, 12C may be arranged in a desired pattern, for example, by using the technique disclosed by Japanese patent application Disclosure No. 1992-317649. According to this technique, the operation of arranging the elastic members so as to extend from around the leg-openings to the side edges of the waist line can be achieved by a relatively simple apparatus and in a single process.

With the disposable diaper according to the invention, the elastic member provided around the left leg-opening further extends to the right side edge of the front and rear bodies and the elastic member provided around the right leg-opening further extends to the left side edge of the front and rear bodies so that a contractile force is exerted over the front and rear bodies toward front and rear waist lines of these bodies and thereby these bodies are brought in close contact with the wearer's skin. As a result, these bodies are free from bagginess.

Relatively inexpensive elastic threads may be used as the elastic members and therefore an increase in the material cost can be alleviated over the case in which the stretchable material is employed for top- and backsheets in order to give the front and rear bodies a desired elasticity.

The elastic members are fed onto the leg-openings as well as onto the front and rear bodies in a single process, so the process can be simplified and thereby the productivity can be improved over the case in which the elastic members are fed onto the leg-openings and onto the front and rear bodies in separate processes.

What is claimed is:

1. A disposable diaper comprising:
   (1) a liquid-permeable topsheet,
   (2) a liquid-impermeable backsheet,
   (3) a liquid-absorbent core sandwiched between said topsheet and said backsheet, said topsheet and backsheet and core connected together to define a front body and a rear body at opposite ends thereof with a crotch zone therebetween, said front and rear bodies defining a waist-opening when the diaper is worn and said crotch zone defining first and second leg-openings when the diaper is worn, and (4) elastic members provided around said waist-opening and the first and second leg-openings,
      a. said elastic members provided around said first and second leg-openings comprising a first elastic member and a second elastic member, respectively, including a plurality of elastic threads extending in parallel with one another from opposite longitudinal side edges of the crotch zone into the front and rear bodies, and
      b. said first elastic member associated with the first leg-opening further extending along a curved course into said front and rear bodies and terminating at one longitudinal side edge of said front and rear bodies while said second elastic member associated with the second leg-opening extends along a curved course into said front and rear bodies and crosses said first elastic member on longitudinal center areas of said front and rear bodies so that said first and second elastic members define a loop-shaped seal surrounding a central zone of said diaper and terminates at the other longitudinal side edge of said front and rear bodies.

2. A disposable diaper according to claim 1, wherein an interthread spacing of the plural elastic threads of each said first and second elastic members progressively widens in the direction of the respective side edges of said front and rear bodies.

3. A disposable diaper according to claim 1, wherein an elongation stress of portions of said first and second elastic members extending over said crotch zone is adjusted to be higher than those of portions of said first and second elastic members extending over said front and rear bodies.

* * * * *